US00PP18733P3

(12) United States Plant Patent
Conibear

(10) Patent No.: US PP18,733 P3
(45) Date of Patent: Apr. 15, 2008

(54) ***LUPINUS* PLANT NAMED 'PERSIAN SLIPPER'**

(50) Latin Name: *Lupinus hybridus*
Varietal Denomination: Persian Slipper

(76) Inventor: Sarah Frances Conibear, West Country Nurseries Donkey Meadow, Woolsery, Bideford, Devon EX39 5QH (GB)

( * ) Notice: Subject to any disclaimer, the term of this patent is extended or adjusted under 35 U.S.C. 154(b) by 0 days.

(21) Appl. No.: 11/474,101

(22) Filed: Jun. 23, 2006

(65) Prior Publication Data

US 2007/0300344 P1 Dec. 27, 2007

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

USDA Plants Databaes for Lupinus hybridus Lem. [online ], [retrieved on Jul. 23, 2007 ]. Retrieved from the Internet <http://plants.usdagov/java/sp/classification_print_friendly.jsp?fileNamePF=cl. . . >one page.*

* cited by examiner

*Primary Examiner*—Kent Bell
*Assistant Examiner*—June Hwu
(74) *Attorney, Agent, or Firm*—The Webb Law Firm

(57) ABSTRACT

'Persian Slipper' is a new variety of *Lupinus hybridus* that exhibits numerous and large-shaped violet-colored flowers.

2 Drawing Sheets

Botanical classification: *Lupinus hybridus*.
Varietal denomination: 'Persian Slipper'.

BACKGROUND OF THE INVENTION

The present invention comprises a new and distinct cultivar of *Lupinus hybridus* known by the varietal name 'Persian Slipper'. The new variety was developed in Great Britain. The new variety is a result of cross breeding Russell Hybrid *Lupinus* Seedling #WCL 066/96 (female parent) (unpatented) and an unknown *Lupinus* male parent (unpatented). The purpose of the breeding program was to develop a cultivar that exhibited improved color, habit, and bloom form from other *Lupinus* varieties known to the breeder. The new variety is similar in growth habit to its female parent, but differs in flower color. The new variety is similar in flower color to *Lupinus hybridus* 'The Governor', but has a more vigorous growth habit, larger flower bells, and more closely packed flower bells. The new variety was first asexually reproduced by basal cuttings/tissue culture in Great Britain. The new variety has been trial and field tested and has been found to retain its distinctive characteristics and remain true to type through successive asexual propagations. Characteristics that distinguish the new variety from others known to the breeder include:

- Clear and intense flower color;
- Flower form — papilionaceous with large flowers; and
- Vigorous growth habit.

The new variety was grown in open soil with additional organic fertilizer applied. The new variety initiates and develops roots in 21 days at 15° C. A finished and flowering plant is produced in 36 weeks in a 21 cm container. The new variety exhibits sparse, but thick roots, that exhibit some branching.

DESCRIPTION OF THE DRAWINGS

The accompanying photographic drawings illustrate the new variety, with the color being as nearly true as it possible with color illustrations of this type.

DESCRIPTION OF THE PLANT

Figure 1:
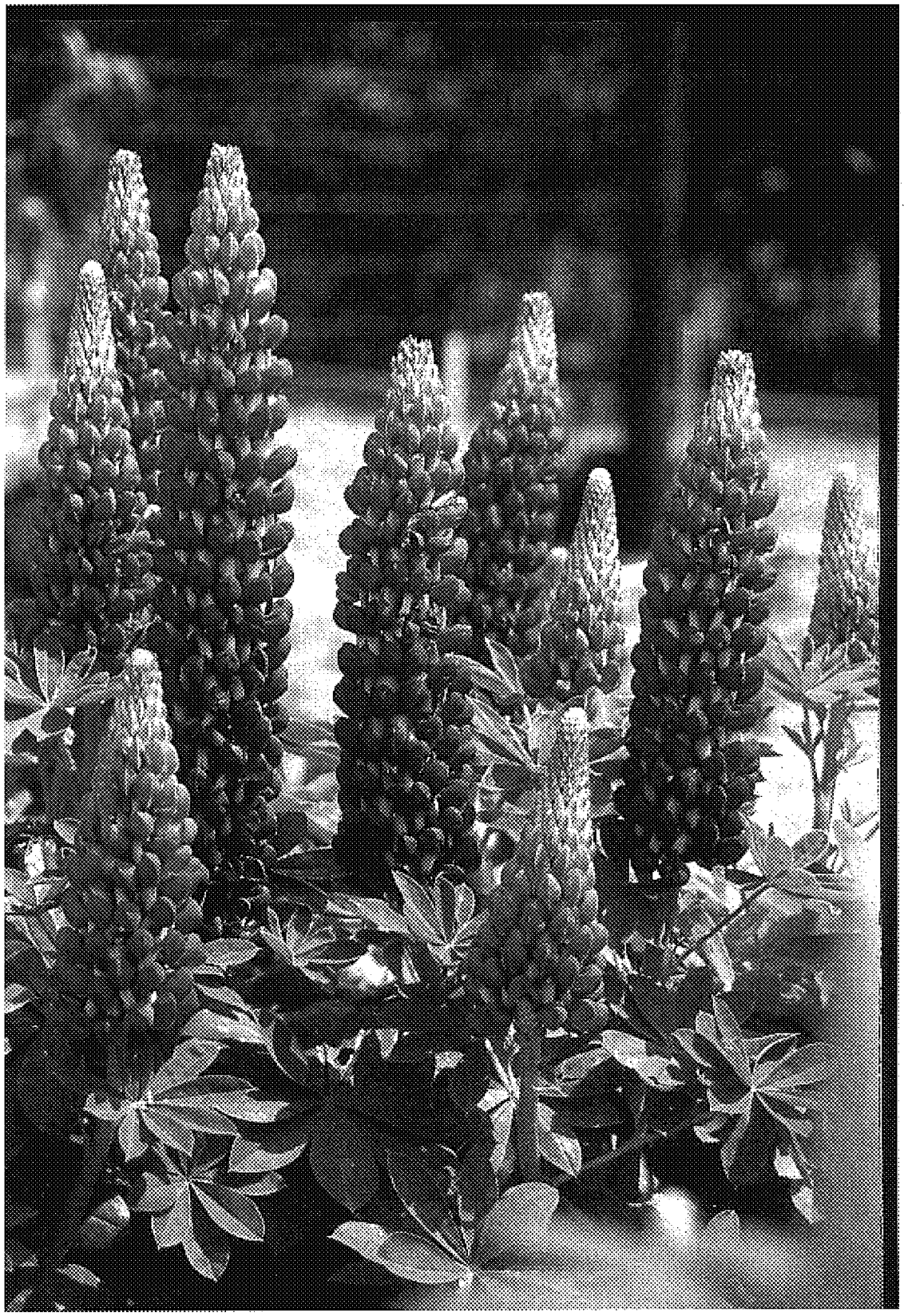
FIG. 1 is a photographic image of multiple plants of the new variety.
Figure 2:
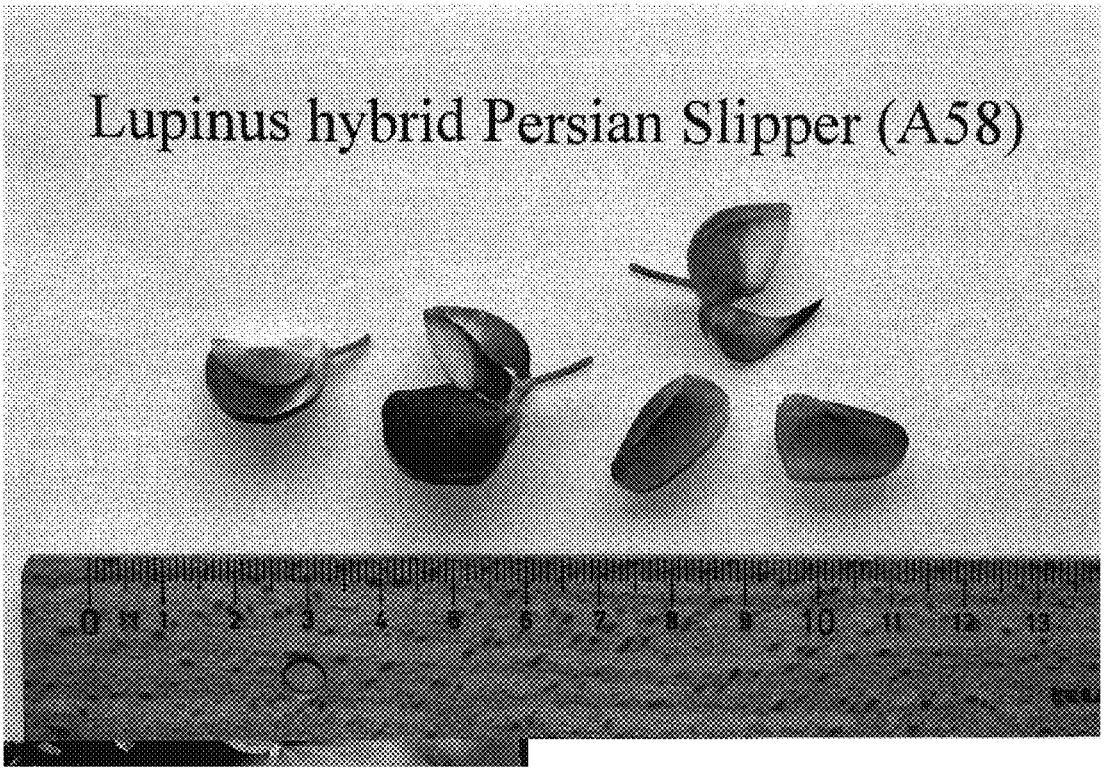
FIG. 2 is a close-up photograph of the petals of the new variety.

The following detailed description sets forth the characteristics of the new cultivar. The data which defines these characteristics were collected by asexual reproductions carried out in Great Britain. The color readings were taken outside under natural daylight. Color references are primarily to the R.H.S. Colour Chart of The Royal Horticultural Society of London.

PLANT

Form: Mounded and symmetrical.
Stem:
- *Diameter.*—15 mm.
- *Color.*—Between 144A and 144B and flushed with a color between 59B and 59C.
- *Texture.*—Slightly hirsute, smooth with longitudinal ridges.
- *Pubescence.*—Slight to medium.

Height: 70 cm.
Vigor: Good.
Branching habit: Free.
Lateral branches:
- *Diameter.*—10–12 mm.
- *Internode length.*—3.5 mm.
- *Texture.*—Lightly hirsute, smooth with longitudinal ridges.
- *Pubescence.*—Present.
- *Color.*—144A.

Foliage:

*Arrangement.*—Ascending spiral.

*Length of leaf stalk.*—Basal foliage: 28 cm. Stem foliage: 17 cm.

*Size of leaf* (*overall*).—Length: 15.5 cm. Width: 15.5 cm.

*Leaflets.*—Shape of leaflet: Oblanceolate. Number: 14. Width: 2.6 cm. Length: 8.0 cm. Shape of apex: Acuminate. Shape of base: Cuneate. Aspect: Horizontal presentation. Margin type: Smooth; entire. Pubescence: Upper surface: None present. Lower surface: Slight. Color: Young leaflet: Upper surface: 137B. Lower surface: 137C. Mature leaflet: Upper surface: 137A. Lower surface: 137B. Petiole: Shape: Flattened and round. Length: Basal leaf: 28 cm. Stem leaf: 17 cm. Diameter: 5 mm. Color: Between 144A and 144B. Venation: Central; mid-rib; the upper surface color is between 137C and 137D; the lower surface is 138B.

FLOWER

Bud (described when buds where just beginning to open):

*Shape.*—Napiform.

*Diameter.*—11 mm.

*Length.*—18 mm.

*Color.*—96C and suffused with a color between 78B and 78C.

Natural flowering season: May through July in The Netherlands.

Flower type and habit: Spike.

*Number of flowers per spike.*—193.

*Length of spike.*—42 cm.

*Diameter of spike.*—10.5 cm.

Corolla:

*Form.*—Zygomorphic

*Petals.*—Standard Petals: Number: 2-fused. Length: 16 mm. Width: 11 mm. Shape: Ovate. Aspect: Parallel to spike. Margin: Smooth and entire. Wing Petals: Number: 2. Length: 19 mm. Width: 11 mm. Shape: Ovoid to kidney-shaped. Aspect: Slightly tilted upward. Margin: Smooth and entire. Keel Petals: Number: 2-fused. Length: 16 mm. Width: 8 mm. Shape: Lingulate. Aspect: Located within wing petals and pointing upwards. Margin: Smooth and entire. Texture and appearance: Smooth and satin-like. Wing Petal Color: When opening: Upper surface: 83C, flushed with a color between 83A and 83B. Lower surface: 85B, flushed with 83D. Fully opened: Upper surface: 83B with an overlay of 83A. Lower surface: 83D. Standard Petal Color: When opening: Upper surface: 155D, edged with 83C. Lower surface: 155D, edged with 85B. Fully opened: Upper surface: 155D, edged with 83B. Lower surface: 155D, edged with 85B. Keel Petal Color: When opening: Upper surface: 85B, flushed with 83C. Lower surface: 85C, flushed with 83C. Fully opened: Upper surface: 85B, flushed with 83C. Lower surface: 85C, flushed with 83C. Keel tip color: 93C.

*Throat* (*visible when the standard petals are parted from the keep petals*): Color: 4D, flushed with 4B. Texture: Smooth and satin-like.

Calyx:

*Form.*—Two unequal halves.

*Length.*—6 mm.

*Diameter.*—4 mm.

*Sepal shape.*—Elliptic.

*Sepal margin.*—Entire.

*Sepal texture.*—Smooth with slight pubescence.

*Sepal size.*—Length: 4 mm. Width: 2.5 mm.

*Sepal color.*—Upper surface: 85D, flushed with 85C. Lower surface: 85D, flushed with 85C.

Fragrance: Slight.

Disease resistance/susceptibility: Susceptible to powdery mildew.

Temperature tolerance: Medium to good.

Lasting quality: Medium to good.

REPRODUCTIVE ORGANS

Stamens:

*Number* (*per flower*).—There are two groups. A first group with 6 stamens and a second group with 4 stamens.

*Filaments.*—Length: First group: 4 mm. Second group: 11 mm. Fused: Yes.

*Anthers.*—Shape: Pencil-like. Length: 2 mm. Color: 31A.

*Pollen.*—Color: 31A. Amount: Plentiful.

Pistils:

*Length.*—13 mm.

*Style.*—Length: 13 mm. Color: 150C.

*Stigma.*—Shape: Spherical. Color: 150C.

Seed/Fruit production:

*Description of conditions when produced.*—Produced freely.

*Color.*—165A.

*Size.*—1.0 mm.

*Number.*—Approximately 2000 per plant.

I claim:

1. A new and distinct variety of *Lupinus hybridus* plant named 'Persian Slipper' as is herein described and illustrated.

* * * * *